(12) United States Patent  
Agarwal et al.

(10) Patent No.: US 9,040,242 B2  
(45) Date of Patent: May 26, 2015

(54) METHOD TO AMPLIFY NUCLEIC ACIDS TO GENERATE FLUORESCENCE LABELED FRAGMENTS OF CONSERVED AND ARBITRARY PRODUCTS

(75) Inventors: Anjana Agarwal, Wilmington, DE (US); Mark A. Jensen, West Chester, PA (US)

(73) Assignee: E I DUPONT DE NEMOURS AND COMPANY DE (US)

(*) Notice: Subject to any disclaimer, the term of this patent is extended or adjusted under 35 U.S.C. 154(b) by 147 days.

(21) Appl. No.: 13/553,256

(22) Filed: Jul. 19, 2012

(65) Prior Publication Data

US 2013/0029341 A1  Jan. 31, 2013

Related U.S. Application Data

(60) Provisional application No. 61/511,367, filed on Jul. 25, 2011.

(51) Int. Cl.
*C12Q 1/68* (2006.01)
*C12P 19/34* (2006.01)

(52) U.S. Cl.
CPC .............. *C12Q 1/689* (2013.01); *C12Q 1/686* (2013.01); *C12Q 1/6846* (2013.01)

(58) Field of Classification Search
CPC .......... C12Q 1/68; C12Q 1/683; C12Q 1/686; C12Q 1/689; C12Q 1/6846
See application file for complete search history.

(56) References Cited

U.S. PATENT DOCUMENTS

| | | |
|---|---|---|
| 5,126,239 A | 6/1992 | Livak et al. |
| 5,753,467 A | 5/1998 | Jensen et al. |
| 6,284,466 B1 | 9/2001 | Benson |
| 2009/0305235 A1 | 12/2009 | Cunningham |

OTHER PUBLICATIONS

Zootecnia et al., "Random amplified polymorphic DNA (RAPD) interpretation requries a sensitive method for the detection of amplified DNA," Electrophoresis, 1996, vol. 17, pp. 1553-1554.*
Grundmann et al., "Automated laser fluorescence analysis of randomly amplified polymorphic DNA: a rapid method for investigating nosocomial transmission of *Acinetobacter baumannii*," J. Med. Microbiol., 1995, vol. 43, pp. 446-451.*
Jorgenson et al., Capillary Electrophoresis: An Introduction, Methods 4:179-90 (1992).
Williams et al., DNA polymorphisms amplified by arbitrary primers are useful as genetic markers, Nucleic Acids Res. 18:6531-34 (1990).
Chang et al: "FluoMEP: A new genotyping method combining the advantages of randomly amplified polymorphic DNA and amplified fragment length polymorphism", Electrophoresis, vol. 28, No. 4, pp. 525-534, Feb. 1, 2007.
Cladera, et al., "Comparative Genetic Diversity of *Pseudomonas stutzeri* Genomovars, Clonal Structure, and Phylogeny of the Species", Journal Of Bacteriology, vol. 186, No. 16, pp. 5239-5248, Aug. 3, 2004.
El Aila, et al., Identification and genotyping of bacteria from paired vaginal and rectal samples from pregnant women indicates similarity between vaginal and rectal microflore, BMC Infectious Diseases, Biomed Central, vol. 9, No. 1, pp. 167-179, Oct. 14, 2009.
Jensen et al., "Use of Homoduplex Ribosomal DNA Spacer Amplification Products and Heteroduplex Cross-Hybridization Products in the Identification of *Salmonella* Serovars", Applied and Environmental Microbiology, pp. 2741-2746 , Aug. 1, 1996.
Li et al., "Bacterial strain typing in the genomic era", FEMS Microbiology Reviews, vol. 33, No. 5, pp. 892-916, Sep. 1, 2009.
Postlethwait et al., "Using random amplified polymorphic DNAs in zebrafish genomic analysis.", Methods In Cell Biology, vol. 60, pp. 165-179, 1999.
Valentini et al., "Random amplified polymorphic DNA (RAPD) interpretation requires a sensitive method for the detection of amplified DNA", Electrophoresis, vol. 17, No. 10, pp. 1553-1554, Jan. 1, 1996.
Corresponding International Search Report and Written Opinion in PCT/US2012/047376, mailed Oct. 8, 2012.

* cited by examiner

*Primary Examiner* — Young J Kim

(57) ABSTRACT

Disclosed herein are methods for the identification of the species, serotype, and strain of a microorganism. Also disclosed are primers for use in detecting such microorganisms and kits comprising such primers.

8 Claims, 4 Drawing Sheets

METHOD TO AMPLIFY NUCLEIC ACIDS TO GENERATE FLUORESCENCE LABELED FRAGMENTS OF CONSERVED AND ARBITRARY PRODUCTS

CROSS-REFERENCE TO RELATED APPLICATION

This application claims priority to U.S. Provisional Application Ser. No. 61/511,367, filed Jul. 25, 2011, which is incorporated herein by reference in its entirety.

FIELD OF INVENTION

The field relates to methods of microorganism identification using random amplified polymorphic DNA (RAPD) PCR.

BACKGROUND OF INVENTION

The experimental approach of using short, conserved ribosomal primers to generate both conserved rDNA fragments and arbitrary amplification products is presented in U.S. Pat. No. 5,753,467. Microbial identification at the level of genus and species is accomplished by the characterization of variations in length and number of fragments located between highly conserved rDNA sequences. The level of identification is extended to the level of serotype and strain by the concurrent amplification of additional arbitrary regions of the microbial genome. These arbitrary amplification events are referred to as Random Amplified Polymorphic DNA (RAPD).

The advantage of this approach is that the same group of primers are used for all species of microorganism to generate amplification products. Since the sequences of these primers are highly conserved among prokaryotic organisms, these primers are generically applied. A substantial savings of time and expense is realized because the necessity for screening or presumptive identification has been eliminated.

The rDNA genetic locus is a genetic unit, which is found in prokaryotic cells. The conserved amplification targets are those sequences found in the spacer region between the 16S and 23S regions of the rDNA genetic locus. These targets are amplified from conserved sequences in the adjacent 16S and 23S regions. Significant portions of the nucleic acid sequence, which make up this genetic locus, are common to all prokaryotic organisms (FIG. 1 shows a generalized schematic of this locus). The overall relatedness of the 16S, 23S, and 5S regions of this genetic locus has been used as a tool to classify differing species of prokaryotes.

The approach described in U.S. Pat. No. 5,753,467 makes use of short primers of 10-12 bases in length. The products generated by these primers are separated through the use of an electrophoretic separation in either agarose or polyacrylamide. The fragments are then visualized through staining with ethidium bromide. During the gel loading process, the PCR products could potentially contaminate the laboratory environment.

SUMMARY OF INVENTION

One aspect is for a method for the identification of the species, serotype, and strain of a microorganism comprising: (a) amplifying DNA comprising variable sequences interspersed between highly conserved rDNA sequences by PCR and amplifying additional genomic sequences by random amplified polymorphic DNA (RAPD) PCR using a first primer of 13-15 bases in length and a second primer of 11-13 bases in length, said first primer comprising: (i) at least 11 contiguous bases from a highly conserved 16S rDNA region; and (ii) a fluorescent label; and (b) separating the amplified DNA produced in step (a).

Another aspect is for an isolated polynucleotide selected from the group consisting of SEQ ID NO:1, SEQ ID NO:2, SEQ ID NO:3, SEQ ID NO:4, and the full-length complements thereof.

A further aspect is for a kit comprising a set of primers comprising PCR primers SEQ ID NO:2 labeled with a fluorophore and at least one of SEQ ID NO:3 and SEQ ID NO:4.

Other objects and advantages will become apparent to those skilled in the art upon reference to the detailed description that hereinafter follows.

BRIEF DESCRIPTION OF THE BIOLOGICAL SEQUENCES

Figure 1:
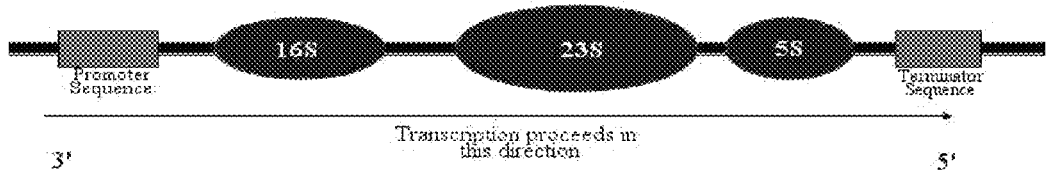
FIG. 1 is a schematic of an rDNA operon disclosed herein.

The following sequences comply with 37 C.F.R. §§1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the European Patent Convention (EPC) and the Patent Cooperation Treaty (PCT) Rules 5.2 and 49.5(a-bis), and Section 208 and Annex C of the Administrative Instructions. The symbols and format used for nucleotide and amino acid sequence data comply with the rules set forth in 37 C.F.R. §1.822.

SEQ ID NO:1 is a forward primer containing an 11 bp sequence from 16S rDNA.
SEQ ID NO:2 is a forward primer containing SEQ ID NO:1 plus two extra nucleotides at the 5' end.
SEQ ID NO:3 is a reverse primer containing 11 bp from 23S rDNA.
SEQ ID NO:4 is a reverse primer containing 13 bp from 23S rDNA.
SEQ ID NO:5 is a forward primer containing 17 bp from 16S rDNA.
SED ID NO:6 is a reverse primer containing 17 bp from 23S rDNA.

DETAILED DESCRIPTION OF PREFERRED EMBODIMENTS

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

In this disclosure, a number of terms and abbreviations are used. The following definitions apply unless specifically stated otherwise.

As used herein, the articles "a", "an", and "the" preceding an element or component of the invention are intended to be nonrestrictive regarding the number of instances (i.e., occurrences) of the element or component. Therefore "a", "an" and "the" should be read to include one or at least one, and the singular word form of the element or component also includes the plural unless the number is obviously meant to be singular.

The term "comprising" means the presence of the stated features, integers, steps, or components as referred to in the claims, but does not preclude the presence or addition of one or more other features, integers, steps, components or groups thereof. The term "comprising" is intended to include embodiments encompassed by the terms "consisting essentially of" and "consisting of". Similarly, the term "consisting essentially of" is intended to include embodiments encompassed by the term "consisting of".

As used herein, the term "about" modifying the quantity of an ingredient or reactant employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like.

The terms "amplification" or "amplify" as used herein include methods for copying a target nucleic acid, thereby increasing the number of copies of a selected nucleic acid sequence. Amplification may be exponential or linear. A target nucleic acid may be either DNA or RNA. The sequences amplified in this manner form an "amplicon".

The term "nucleic acid" refers to a polymer of ribonucleic acids or deoxyribonucleic acids, including RNA, mRNA, rRNA, tRNA, small nuclear RNAs, cDNA, DNA, PNA, RNA/DNA copolymers, or analogues thereof. Nucleic acids may be obtained from a cellular extract, genomic (gDNA) or extragenomic DNA, viral RNA or DNA, or artificially/chemically synthesized molecules.

The term "complementary" refers to nucleic acid sequences capable of base-pairing according to the standard Watson-Crick complementary rules, or being capable of hybridizing to a particular nucleic acid segment under relatively stringent conditions. Nucleic acid polymers are optionally complementary across only portions of their entire sequences.

The term "target", "target sequence", or "target nucleotide sequence" refers to a specific nucleic acid sequence, the presence, absence or abundance of which is to be determined.

As used herein, a "primer" for amplification is an oligonucleotide that is complementary to a target nucleotide sequence and leads to addition of nucleotides to the 3' end of the primer in the presence of a DNA or RNA polymerase. The 3' nucleotide of the primer should generally be identical to the target sequence at a corresponding nucleotide position for optimal expression and amplification. The term "primer" as used herein includes all forms of primers that may be synthesized including peptide nucleic acid primers, locked nucleic acid primers, phosphorothioate modified primers, labeled primers, and the like. As used herein, a "forward primer" is a primer that is complementary to the anti-sense strand of dsDNA. A "reverse primer" is complementary to the sense-strand of dsDNA. Primers are typically between about 10 and about 100 nucleotides in length, preferably between about 15 and about 60 nucleotides in length, and most preferably between about 20 and about 30 nucleotides in length.

An oligonucleotide (e.g., a probe or a primer) that is specific for a target nucleic acid will "hybridize" to the target nucleic acid under suitable conditions. As used herein, "hybridization" or "hybridizing" refers to the process by which an oligonucleotide single strand anneals with a complementary strand through base pairing under defined hybridization conditions. "Specific hybridization" is an indication that two nucleic acid sequences share a high degree of complementarity. Specific hybridization complexes form under permissive annealing conditions and remain hybridized after any subsequent washing steps. Permissive conditions for annealing of nucleic acid sequences are routinely determinable by one of ordinary skill in the art and may occur, for example, at 65° C. in the presence of about 6×SSC. Stringency of hybridization may be expressed, in part, with reference to the temperature under which the wash steps are carried out. Such temperatures are typically selected to be about 5° C. to about 20° C. lower than the thermal melting point (Tm) for the specific sequence at a defined ionic strength and pH. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of conditions uses higher temperatures in which the washes are identical to those above except for the temperature of the final two 30 min washes in 0.2×SSC, 0.5% SDS was increased to 60° C. Another preferred set of stringent hybridization conditions is 0.1×SSC, 0.1% SDS, 65° C. and washed with 2×SSC, 0.1% SDS followed by a final wash of 0.1×SSC, 0.1% SDS, 65° C.

The term "label" refers to any detectable moiety. A label may be used to distinguish a particular nucleic acid from others that are unlabeled, or labeled differently, or the label may be used to enhance detection.

The term "specimen" means a biological sample such as saliva, stools, urine, blood, gastric biopsy, gastrointestinal tissue, tumor cells, mucus secretions, dental plaque, and other biological tissues; meat products; food products; and environmental samples such as soil or water.

Nucleic Acid Detection

To avoid the potential hazard of laboratory environment contamination, the present method requires the use of fluorescence labeled primers. Products generated from these primers can be directly detected by capillary electrophoresis. Use of short fluorescence labeled primers, 10 to 12 bases, presents a difficulty because the presence of the fluorescent moiety makes such primers a poor substrate for DNA polymerases. Longer primers with 100% homology to the conserved sequences cannot be substituted because such primers will amplify only the ribosomal fragments without the arbitrarily primed pattern elements that are critical to strain level differentiation.

The minimum length required for incorporation of a fluorescence labeled primer was 13 bases. Since 13-base primers with a perfect match to the ribosomal site amplified only the ribosomal fragments, it was necessary to employ a 2-base mismatch on the 5' end of the fluorescence labeled primer.

Since only the last 11 bases matched the ribosomal sequence, such primers are capable of amplifying both ribosomal fragments and arbitrary genomic fragments simultaneously.

More particularly, the present method comprises amplifying DNA comprising variable sequences interspersed between highly conserved rDNA sequences by PCR and amplifying additional genomic sequences by RAPD PCR using a first primer of 13-15 bases in length and a second primer of 11-13 bases in length. The first primer comprises at least 11 contiguous bases from a highly conserved 16S rDNA region and a fluorescent label. In a second step, the method comprises separating the amplified DNA produced in the amplifying step.

The method described herein is useful in identifying a wide variety of microorganisms. Representative but not exhaustive of the many types of organisms including both genus, species and serotype that may be elicited through the use of the present procedures are *Listeria monocytogenes, Listeria welshimeri, Listeria innocua, Listeria ivanovii, Salmonella typhimurium, Salmonella enteritidis, Salmonella newport, Salmonella infantis, Staphylococcus aureus, Staphylococcus scuiri, Staphylococcus warneri, Staphylococcus saprophyticus, Staphylococcus epidermidis, Escherichia coli, Escherichia fergusonii, Escherichia blattae, Escherichia hermanii, Escherichia vulneris, Citrobacter freundii, Citrobacter diversus, Enterobacter aerogenes, Enterobacter agglomerans, Enterobacter cloacae, Proteus mirabilis, Proteus vulgaris,* and *Yersinia enterocolitica*. Such a listing may form a database of previously visualized products which when compared to the electrophoresed, visualized fragment products according to the present method, afford an identification of the species (and the serotype and strain if applicable).

It is readily appreciated by one skilled in the art that the present method may be applied to microorganisms in the context of a wide variety of circumstances. Thus, a preferred use of the present invention is in the identification of microorganisms in food. Additionally, research directed to microbial infections in humans, other animals, and plants would benefit from the procedure herein.

Nucleic acids may be isolated from a sample according to any methods well known to those of skill in the art. If necessary the sample may be collected or concentrated by centrifugation and the like. The cells of the sample may be subjected to lysis, such as by treatments with enzymes, heat, surfactants, ultrasonication, or combination thereof.

Various methods of nucleic acid extraction are suitable for isolating nucleic acids. Suitable methods include phenol and chloroform extraction. See, e.g., Maniatis et al., Molecular Cloning, A Laboratory Manual, 2d, Cold Spring Harbor Laboratory Press (1989).

RAPD PCR is disclosed in U.S. Pat. No. 5,126,239 (see also, Williams et al., Nucleic Acids Res. 18:6531-34 (1990)). The approach describes the use of a small oligonucleotide, i.e., greater than seven nucleotides, of arbitrary composition in a DNA amplification reaction. Short primers are used in order that complementary and reverse complementary sequences to the primer can be found at distances along the genome which are sufficiently small that DNA amplification can take place. The fragments generated in the amplification process are called RAPD markers. These RAPD markers show a size distribution which is sensitive to modest differences in the genomic makeup of the DNA used in the amplification process.

As noted in U.S. Pat. No. 5,753,467, the process of U.S. Pat. No. 5,126,239 requires 45 cycles, which frequently results in the formation of secondary amplification products and nonspecific DNA synthesis. A product profile background which contains high levels of such secondary amplification products and nonspecific DNA can severely restrict the ability of pattern recognition software to compare such a product profile with a known database. The process disclosed herein, however, uses fewer amplification cycles with longer annealing times to produce a far less complex product profile with a significantly reduced nonspecific DNA background.

The skilled artisan is capable of designing and preparing arbitrary primers that are appropriate for RAPD PCR. The length of the amplification primers depends on several factors including the nucleotide sequence identity and the temperature at which these nucleic acids are hybridized or used during in vitro nucleic acid amplification. The considerations necessary to determine a preferred length for an amplification primer of a particular sequence identity are well known to the person of ordinary skill in the art.

Primers that amplify a nucleic acid molecule can be designed using, for example, a computer program such as OLIGO (Molecular Biology Insights, Inc., Cascade, Colo.). Important features when designing oligonucleotides to be used as amplification primers include, but are not limited to, an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). Preferred primers, along with their targets, are described in Table 1 below.

As discussed in U.S. Pat. No. 5,753,467, a significant degree of intramolecular hybridization is known to occur within the rDNA genetic locus. The resulting secondary structure frequently makes it difficult for amplification primers to compete for hybridization sites. In order to enhance the amplification of fragments contained within the rDNA region it is necessary to modify the amplification temperature profile which is typically practiced. The principal modifications consist of the use of substantially longer annealing times, in a range of about 3 to about 7 minutes. Amplification reactions are being run under high stringency conditions in conjunction with a decreased number of amplification cycles. A high stringency amplification is accomplished by running the reaction at the highest annealing temperature where products are reproducibly formed. Use of maximum annealing temperature insures that only the most stable hybridization structures will form and that the areas surrounding the priming sites will possess a minimal amount of secondary structure.

The presence or absence target nucleic acids can determined, e.g., by analyzing the amplified nucleic acid products of the primer extension by size using standard methods, for example, agarose gel electrophoresis, polyacrylamide gel electrophoresis, capillary electrophoresis, pulsed field electrophoresis, denatured gradient gel electrophoresis, DNA microarrays, or mass spectrometry. Preferably, capillary electrophoresis is used to separate the amplified products.

In capillary electrophoresis, the length of a nucleic acid fragment is examined by allowing a sample to migrate through a thin tube filled with gel and measuring a period of time required for the sample to migrate a certain distance (e.g., to the end of a capillary). Upon capillary electrophoresis, it is usual to detect a sample using a fluorescence signal detector that is installed at the end of a capillary.

Apparatuses for carrying out capillary electrophoresis are well-known. Many references are available describing the basic apparatus and several capillary electrophoresis instruments are commercially available, e.g., from Applied Biosystems (Foster City, Calif.). Exemplary references describing capillary electrophoresis apparatus and their operation include Jorgenson, Methods 4:179-90 (1992); Colburn et al., Applied Biosystems Research News, issue 1 (winter 1990); and the like.

With respect to fluorescence measurement, when PCR is performed using primers labeled at their 5' ends with a fluorophore, the amplified target sequence is labeled with the detectable fluorescent material, and the intensity of fluorescence emitted from the fluorescent material is measured using a fluorescence spectrophotometer. Suitable fluorophores include, but are not limited to, 6-FAM; Alexa fluor 405, 430, 488, 532, 546, 555, 568, 594, 633, 647, or 660; Cy2; Cy3; Cy3.5; Cy5; Cy5.5; Cy7; hydroxycoumarin; methoxycoumarin; aminocoumarin; fluorescein; HEX; R-phycoerythrin; rhodamine Red-X; ROX; Red 613; Texas Red; allophycocyanin; TruRed; BODIPY 630/650; BODIPY 650/665; BODIPY-FL; BODIPY-R6G; BODIPY-TMR; BODIPY-TRX; carboxyfluorescein; Cascade Blue; 6-JOE; Lissamine rhodamine B; Oregon Green 488, 500, or 514; Pacific Blue; REG; Rhodamine Green; SpectrumAqua; TAMRA; TET; and Tetramethylrhodamine.

As discussed above, preferred primers are disclosed in Table 1. One embodiment related thereto is for an isolated polynucleotide selected from the group consisting of SEQ ID NO:1, SEQ ID NO:2, SEQ ID NO:3, and SEQ ID NO:4. Another embodiment is for kit comprising a set of primers comprising PCR primers SEQ ID NO:2 labeled with a fluorophore and at least one of SEQ ID NO:3 and SEQ ID NO:4. In some aspects, the kit comprises both PCR primers SEQ ID NOs: 3 and 4.

Such a kit may comprise a carrier being compartmentalized to receive in close confinement therein one or more container means, such as tubes or vials. One of said container means may contain unlabeled or detectably-labeled primers. The primers may be present in lyophilized form or in an appropriate buffer as necessary. One or more container means may contain one or more enzymes or reagents to be utilized in PCR reactions. These enzymes may be present by themselves or in admixtures, in lyophilized form or in appropriate buffers. The kit may also contain some or all the additional elements necessary to carry out the PCR and/or CE, such as buffers, extraction reagents, enzymes, pipettes, plates, nucleic acids, nucleoside triphosphates, filter paper, gel materials, transfer materials, autoradiography supplies, and the like.

GENERAL METHODS

The following examples are provided to demonstrate preferred embodiments. It should be appreciated by those of skill in the art that the techniques disclosed in the examples which follow represent techniques discovered by the inventor to function well in the practice of the methods disclosed herein, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the presently disclosed methods.

The following abbreviations in the specification correspond to units of measure, techniques, properties, or compounds as follows: "sec" or "s" means second(s), "min" means minute(s), "h" or "hr" means hour(s), "μL" means microliter(s), "mL" means milliliter(s), "L" means liter(s), "μM" means micromolar, "M" means molar, "pmol" means picomole(s), "g" means gram(s), "μg" means microgram(s), "ng" means nanogram(s), "pg" means picogram(s), "CE" means capillary electrophoresis, "bp" means basepair(s), "6-FAM" means 6-carboxyfluorescein.

EXAMPLE 1

Initially, amplification reactions were carried out with a 17-mer primer pair (SEQ ID NOs: 5 and 6), one of which contained a 6-FAM fluorescent tag (SEQ ID NO:5), to determine the size distribution of the ribosomal component of the PCR amplification. These fragments provided reference products that made it possible to identify the ribosomal pattern components in the mixed ribosomal and arbitrary amplification.

To generate the ribosomal/RAPD DNA profile, a mixture of three individual primers (one forward and two reverse primers) were used. The forward primer was labeled with 6-FAM dye and contained an 11 bp sequence from 16S rDNA (SEQ ID NO:1) plus two extra nucleotides (CA) added at the 5' end (SEQ ID NO:2). The CA sequence does not match the known conserved 16S ribosomal sequence and serves only to make the fluorescence labeled primer a better substrate for the DNA polymerase. To amplify both ribosomal and RAPD fragments, sequences of both reverse primers were obtained from a single location of 23S rDNA. The sequences of the reverse primers are as follows: R-23S reverse primer 1: SEQ ID NO:3 (11 mer) and R-23S reverse primer 2: SEQ ID NO:4 (13 mer).

TABLE 1

| Primers | |
| --- | --- |
| Location of primers | Sequence 5'-3' |
| 16S-17mer 6-FAM label | (6-FAM)-SEQ ID NO: 5 |
| 23S-17mer | SEQ ID NO: 6 |
| 23S-11mer | SEQ ID NO: 3 |
| 23S-13mer | SEQ ID NO: 4 |
| 16S-13mer 6-FAM | (6-FAM)-SEQ ID NO: 2 |

The PCR reaction was performed in 30 μl of reaction mixture, contained 1×PCR buffer from KAPA 2G robust HotStart ReadyMix (Kapa Biosystems, Woburn, Mass.), 20 pmol of forward primer (6-FAM)-SEQ ID NO:2), 20 pmol of reverse primer1 (SEQ ID NO:3), 4 pmol of reverse primer 2 (SEQ ID NO:4), and 50 pg to 100 ng of gDNA. The PCR fragments were amplified by initial denaturation at 95° C. for 2 min., followed by 35 cycles of (95° C.-30 sec., 45° C.-5 min., and 72° C.-30 sec.). The final extension was performed at 72° C. for 10 min. GeneScan 1200 LIZ® (Applied Biosystems, Carlsbad, Calif.) was used as a DNA size standard and was added in the PCR product after amplification. The PCR fragments were separated and detected using an Applied Biosystem's model 3730 CE instrument. Applied Biosystem PeakScanner software was used to identify fragment peaks in the CE pattern and characterize them.

Figure 2A:
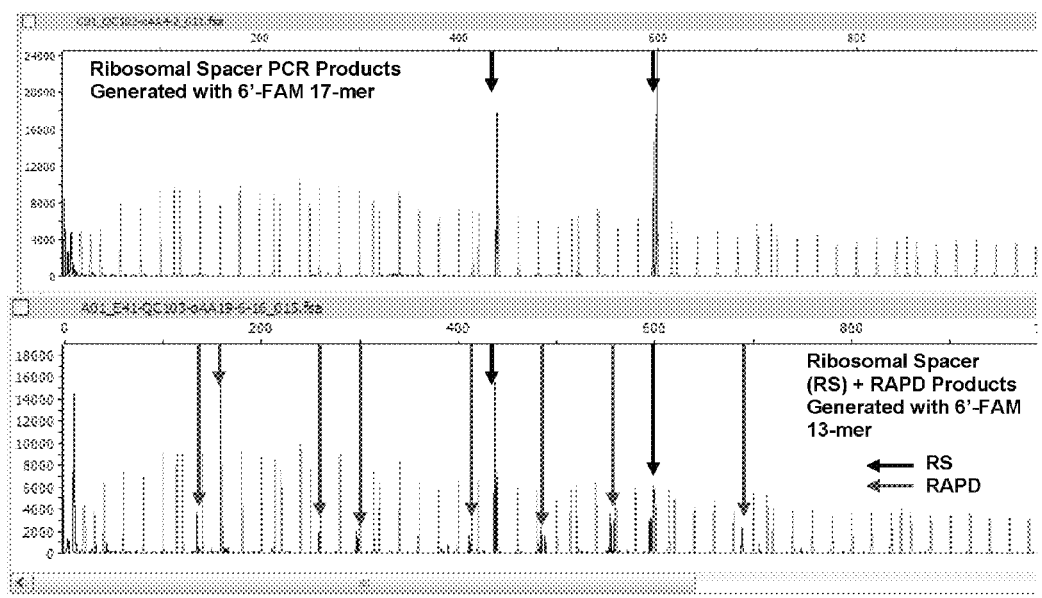
FIG. 2 shows electropherograms of PCR products generated with 6-FAM labeled 17mers alone and the with 6-FAM labeled 13 and 11 mer primer group for *Salmonella infantis*, *Staphylococcus epidermidis*, and *Enterobacter aerogenes*.
Figure 2B:
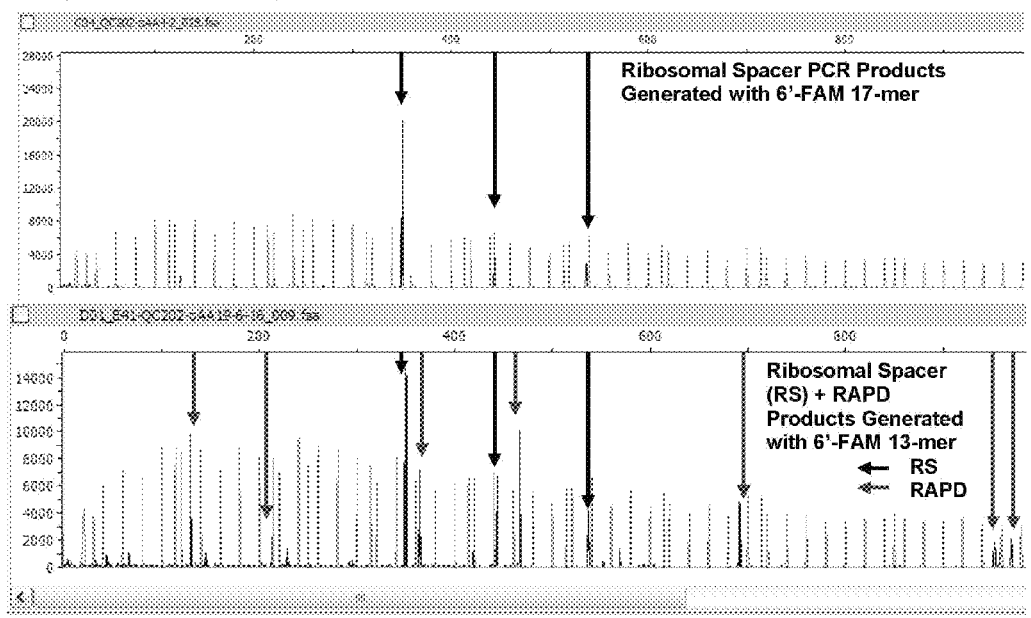
Figure 2C:
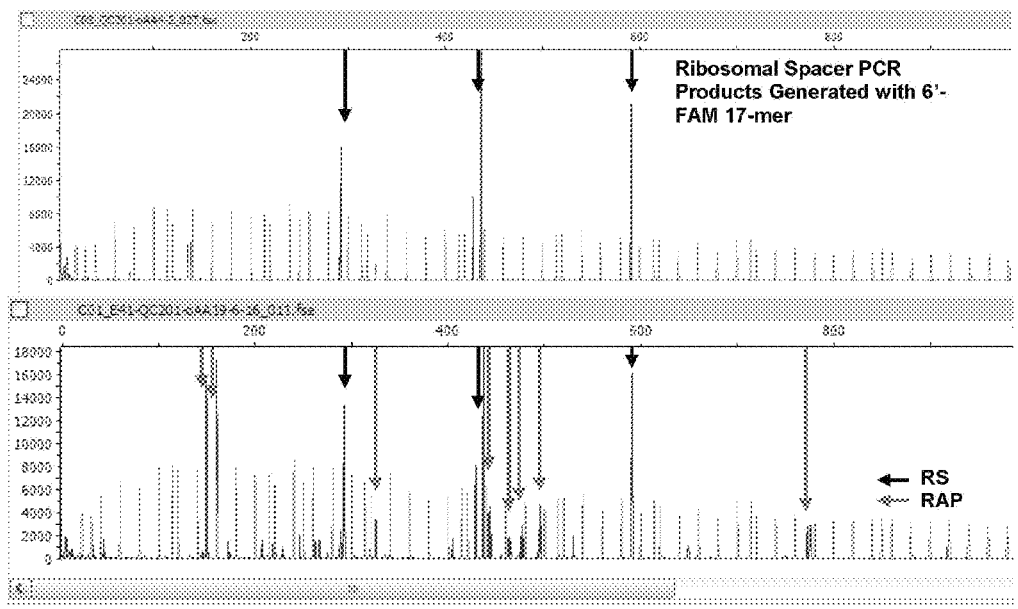

Examples of three amplification reactions are shown in FIG. 2. Reactions were carried out as described in the above PCR protocol for genomic DNA extracts from *Salmonella infantis, Staphylococcus epidermidis*, and *Enterobacter aerogenes*. In FIG. 2, each electropherogram is compared to an electropherogram that contains only the ribosomal spacer fragments. This is done to demonstrate that these ribosomal fragments are preserved in the presence of the arbitrary amplification events and to show that yields of arbitrary and ribosomal fragments were comparable.

The approach of combining 11-base and 13-base primers, one of which contains a fluorescent tag, clearly provides amplification of both ribosomal and RAPD fragments. Under the specified amplification conditions, yields of the ribosomal and dominant RAPD fragments are comparable.

The resulting patterns contain fluorescence labeled fragments that can be separated by capillary electrophoresis to produce a pattern of products that contain both conserved ribosomal fragments and arbitrary RAPD fragments.

What is claimed is:

1. A method for the identification of the species, serotype, and strain of a microorganism comprising:
   (a) amplifying DNA comprising variable sequences interspersed between highly conserved rDNA sequences by PCR and amplifying additional genomic sequences by random amplified polymorphic DNA (RAPD) PCR using a first primer of 13-14 bases in length and a second primer of 11-13 bases in length, said first primer comprising:
      (i) 11-12 contiguous bases from a highly conserved 16S rDNA region;
      (ii) 2 bases at the 5' end of said first primer that are not complementary to said highly conserved 16S rDNA region; and
      (iii) a fluorescent label; and
   (b) separating the amplified DNA produced in step (a).

2. The method of claim 1, wherein said first primer is a forward primer.

3. The method of claim 2, wherein said first primer comprises SEQ ID NO:1.

4. The method of claim 3, wherein said first primer is SEQ ID NO:2.

5. The method of claim 1, wherein said second primer comprises 11-13 contiguous bases from 23S rDNA.

6. The method of claim 5, wherein said second primer is SEQ ID NO:3 or SEQ ID NO:4.

7. The method of claim 1, wherein said amplifying step utilizes a third primer of 11-13 bases in length, said third primer comprising 11-13 contiguous bases from 23S rDNA, wherein said third primer is a different length than said second primer, and wherein one of either the second primer or third primer comprises 13 contiguous bases from 23S rDNA.

8. The method of claim 1, wherein step (b) is accomplished by capillary electrophoresis.

* * * * *

```
                              SEQUENCE LISTING

<160> NUMBER OF SEQ ID NOS: 6

<210> SEQ ID NO 1
<211> LENGTH: 11
<212> TYPE: DNA
<213> ORGANISM: Artificial Sequence
<220> FEATURE:
<223> OTHER INFORMATION: Primer

<400> SEQUENCE: 1
gaagtcgtaa c                                                              11

<210> SEQ ID NO 2
<211> LENGTH: 13
<212> TYPE: DNA
<213> ORGANISM: Artificial Sequence
<220> FEATURE:
<223> OTHER INFORMATION: Primer

<400> SEQUENCE: 2
cagaagtcgt aac                                                            13

<210> SEQ ID NO 3
<211> LENGTH: 11
<212> TYPE: DNA
<213> ORGANISM: Artificial Sequence
<220> FEATURE:
<223> OTHER INFORMATION: Primer

<400> SEQUENCE: 3
aaggcatcca c                                                              11

<210> SEQ ID NO 4
<211> LENGTH: 13
<212> TYPE: DNA
<213> ORGANISM: Artificial Sequence
<220> FEATURE:
<223> OTHER INFORMATION: Primer

<400> SEQUENCE: 4
caaggcatcc acc                                                            13

<210> SEQ ID NO 5
<211> LENGTH: 17
<212> TYPE: DNA
<213> ORGANISM: Artificial Sequence
<220> FEATURE:
<223> OTHER INFORMATION: Primer

<400> SEQUENCE: 5
gtgaagtcgt aacaagg                                                        17

<210> SEQ ID NO 6
<211> LENGTH: 17
<212> TYPE: DNA
<213> ORGANISM: Artificial Sequence
<220> FEATURE:
<223> OTHER INFORMATION: Primer

<400> SEQUENCE: 6
caaggcatcc accgtgt                                                        17
```